(12) United States Patent
Hui et al.

(10) Patent No.: US 8,148,354 B2
(45) Date of Patent: Apr. 3, 2012

(54) USE OF 20(S)-PROTOPANAXADIOL IN MANUFACTURE OF ANTIDEPRESSANTS

(75) Inventors: Yongzheng Hui, Shanghai (CN); Zirong Yang, Shanghai (CN); Zhiqi Yang, Shanghai (CN); Qiang Ge, Shanghai (CN)

(73) Assignee: Shanghai Innovative Research Center of Traditional Chinese Medicine, Shanghai (CN)

( * ) Notice: Subject to any disclaimer, the term of this patent is extended or adjusted under 35 U.S.C. 154(b) by 504 days.

(21) Appl. No.: 12/304,114

(22) PCT Filed: Jun. 8, 2007

(86) PCT No.: PCT/CN2007/001816
§ 371 (c)(1),
(2), (4) Date: Dec. 9, 2008

(87) PCT Pub. No.: WO2007/143930
PCT Pub. Date: Dec. 21, 2007

(65) Prior Publication Data
US 2010/0234624 A1   Sep. 16, 2010

(30) Foreign Application Priority Data
Jun. 9, 2006   (CN) .......................... 2006 1 0027507

(51) Int. Cl.
*A61K 31/56* (2006.01)
*C07J 9/00* (2006.01)
(52) U.S. Cl. ...................................... 514/178; 552/540
(58) Field of Classification Search .................. 514/178; 552/540
See application file for complete search history.

(56) References Cited

U.S. PATENT DOCUMENTS
6,083,932 A   7/2000   Pang et al.

FOREIGN PATENT DOCUMENTS

| CN | 1526407 A | 9/2004 |
|---|---|---|
| CN | 1569882 A | 1/2005 |
| CN | 1615901 A | 5/2005 |
| CN | 1251677 C | 4/2006 |
| CN | 1763069 | 4/2006 |
| CN | 1875975 A | 12/2006 |
| KR | 1020050034354 A | 4/2005 |
| WO | WO 2004100963 A1 * | 11/2004 |
| WO | 2006/115307 A1 | 11/2006 |

OTHER PUBLICATIONS

Lee et al. Planta Med., 2005, vol. 71, pp. 1167-1170.*
European Journal of Pharmaceutical Sciences, 1995, vol. 3, pp. 77-85.*
Ostacher, M.J. J. Clin. Psychiatry, 2006, vol. 67, Suppl. 11, pp. 18-21, abstract only used in rejection.*
International Search Report for International Application No. PCT/CN2007/01816 dated Sep. 20, 2007, 4 pages.
Hu Jing et al., "Study on Anti-depression of Tricyclic Drug and Ginseng Saponin," Hei Long Jiang Medical Journal, 2003, 27 (4): 268-269.
Tode T. et al., "Effect of Korean Red Ginseng on Psychological Functions in Patients with Severe Climacteric Syndromes," International Journal of Gynecology & Obstetrics 1999, 67: 169-174.
Kuribara Hisashi et al., "An Antidepressant Effect of Sho-ju-sen, a Japanese Herbal Medicine, Assessed by Learned Helplessness Model in Mice," Phytother. Res. 2004, 18: 173-176.
Li Jianmei et al., "Progress of Studies on Traditional Chinese Medicine for Treating Depression and Anxiety Disorders," China Journal of Chinese Materia Medica, 2001, 26 (12): 805-807.
Wang Junmo, "Progress of Studies on the Pharmacology of Panax Ginseng," Studies on Panax Ginseng, 2001, 13 (3): 2-10.
Zhou, Chenglin; Ma, Qiang; Xie, Yeqi; Study on the effect of panaxdiol and panaxtriol of American Ginseng Diol in terms of students' intelligence and emotion; Journal of Shenyang Institute of Physical Education, Mar. 1998, China.

* cited by examiner

*Primary Examiner* — Sreeni Padmanabhan
*Assistant Examiner* — Samira Jean-Louis
(74) *Attorney, Agent, or Firm* — Perkins Coie LLP; Yingli Wang

(57) ABSTRACT

The invention provides the novel use of 20(S)-protopanaxadiol in the preparation of medicaments for the treatment of depressive psychiatric disorders. The pharmacological test results indicated that the compound could remarkably increase the level of NE, 5-HT and HAV in the brains of model rats having depressive disorders, remarkably enhance tremors induced by 5-hydroxytryptophan (5-HTP) and behavioral effects induced by levodopa, and inhibit the reuptake of 5-HT and NA.

20 Claims, No Drawings

USE OF 20(S)-PROTOPANAXADIOL IN MANUFACTURE OF ANTIDEPRESSANTS

FIELD OF THE INVENTION

This invention pertains to medicines, in particular, to the application of 20(S)-protopanaxadiol in the preparation of antidepressants.

BACKGROUND OF THE INVENTION

Depression is a common, frequently-occurring disease which poses a threat to human health. It is characterized by depressive emotions and falls into the psychiatric category of affective disorders. The signs of depression include low mood, slow thinking and distress. The principal disturbances are feelings of sadness, despair, worthlessness and helplessness, and a loss of interest or pleasure in daily activities. Psychologically, it may be accompanied by anxiety, feelings of guilt, delusion and hallucinations, decreased concentration and memory as well as suicide attempts. The physical signs are sleep disturbance, appetite loss, weight loss, sexual hypoactivity, restlessness and fatigue.

The development of depression is slow, generally, lasting for weeks or months. Some patients whose illness is induced by psychological and social factors may have acute symptoms. In the initial phase, patients usually suffer from insomnia, poor appetite, lethargy and decreased working efficiency. Later, symptoms include distress and despair, even thoughts of suicide may gradually occur.

It is reported that during their lifetime, 6-8% of people in western developed countries suffer from depression which is a common psychiatric disease. As the population has aged, the incidence has increased to 20-50% among people over the age of 60. Statistics indicate that the incidence of depression in the U.S. is second only to that of heart disease and has an annual cost of $44 billion. Depression is fast becoming a serious global problem as well.

In China, due to the acceleration of the pace of life and the increasing intensity of various pressures, the incidence of mental illness has been rising annually. The diagnosis of depression and therapies for treating it are attracting the attention of communities and primary clinical institutions as well as patients. Currently, patients with depression account for 20-30% of the total population of psychiatric wards. It is estimated by experts that the proportion of depression patients treated in China will increase from 25% at present to 40% in 2010. More women experience depression than men probably due to a heavier burden from daily life and a longer exposure to unpredictable stressors. The incidences of depression are high among the population but the causes of depression are not clear. It may involve a combination of social, psychological, genetic, and biochemical imbalances as well as neuroendocrine changes. The present domestic market scale for antidepressants in China is very small, but grows very fast. Hence, the market for antidepressants has great potential for developers of new drugs.

Currently, depression is mainly treated by administration of antidepressants. In the 1950s, the first drug developed for the treatment of depression was monoamine oxidase inhibitor (MAOI). Due to the severity of its adverse effects, it was replaced by tricyclic antidepressants (TCAs). Selective serotonin re-uptake inhibitors (SSRIs) are at present the chiefly-prescribed drugs. Compared with the first generation of antidepressants, the second generation drugs are safer and better tolerated. Although TCAs such as imipramine, amitriptyline, doxepin, chlorimipramine, desipramine and protriptyline are effective and curative, they are less safe. And overdosing causes higher mortality. These drugs often cause such side effects as symptoms of cardiovascular toxicity, over-mitigation and high levels of anti-cholinergics. Moreover, they act with slow efficacy and multiple doses must be taken daily for a long period, so patients do not become overly reliant on them. Patients administered SSRIs show better tolerance and fewer side effects, especially less cardiovascular toxicity and lower anti-cholinergic concentration, but can develop stomach and intestinal problems as well as sexual disturbances. Higher occurrence of over-mitigation, dry mouth and constipation is observed when paroxetine is used. Higher occurrence of anxiety, restlessness, anorexia and insomnia is observed when fluoxitine is used. Higher occurrence of diarrhea is observed when zoloft is used. Currently, there is no ideal antidepressant that has only minor side effects, even when used in combination with other medicines, and is safe when used at a stronger than recommended dose.

Moreover, after administration of an SSRI, the most commonly-prescribed drug, many patients suffer from uncomfortable stomach and intestinal problems. Sleep and sexual disturbances are more prevalent than with administration of TCAs. The "5-HT syndrome" has drawn particular interest. This syndrome is induced by over-stimulation of the receptor 5-HT1A in the brain stem, and the clinical signs include myoclonus, hyperpyrexia, high blood pressure and even death. It is reported that patients have a greater tendency to commit suicide after administration of certain antidepressants. Therefore, the development of a natural antidepressant with better safety and efficacy is of the highest priority.

Protopanaxadiols are aglycone of panaxadiol saponins. They consist of 20(S)-protopanaxadiol and 20(R)-protopanaxadiol which constitute an enantiomer pair. Their structures are shown below:

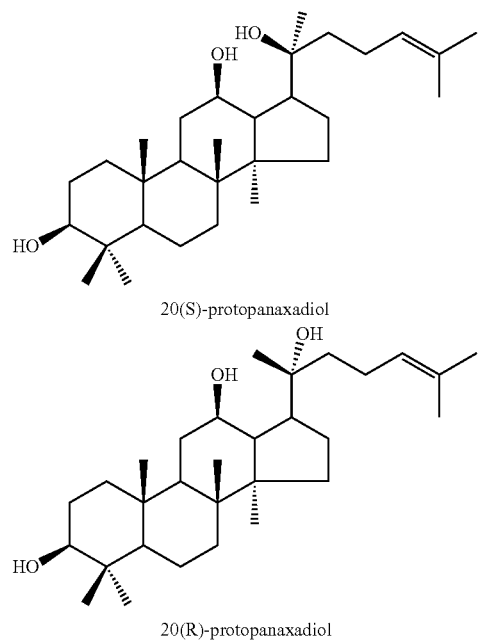

20(S)-protopanaxadiol

20(R)-protopanaxadiol

20(S)-protopanaxadiol is a principal aglycone of panaxadiol saponins. Chinese patent applications Nos. 02146549.5 and 200410002109.5 report its anti-tumor activity, but there is no prior report with its anti-depression activity.

BRIEF SUMMARY OF THE INVENTION

The present invention provides an application of 20(S)-protopanaxadiol in the manufacture of medicaments for the treatment of depressive psychiatric disorders.

We employ the total saponin extracts from plants or leaves of the ginseng family, or gold theragran P.E. extracts as the source material. After oxidative alkaline hydrolysis in organic solvents, 20(S)-protopanaxadiol of high yield and purity is obtained by column chromatography purification. This process has been granted a Chinese invention patent (Patent No.: 2004100180388).

The present invention relates to the use of 20(S)-protopanaxadiol in the manufacture of medicaments for the treatment of depressive psychiatric disorders.

The above-mentioned 20(S)-protopanaxadiol is used in preparation of medicaments for the treatment of depressive psychiatric disorders in mammals including human beings.

Depressive psychiatric disorders to which this invention is applicable is manifested by basic symptoms of a persistent lowering of mood, a loss of interest in usual activities and a diminished ability to experience pleasure. The psychological symptoms include anxiety, feelings of guilt, psychiatric signs (delusion and hallucination), cognitive disorders (reduced concentration and memory), suicidal thoughts and actions, psychomotor retardation or elation. Physical symptoms include sleep disorder, appetite disturbance, sexual function hypoactivity, fatigue or greater severity of symptoms in mornings than in evenings.

Depressive psychiatric disorders according to the 10th edition of International Classification of Diseases (ICD-10) include depressive episode, recurrent depression, bipolar affective disorder and persistent affective disorder. There are mild, intermediate and severe types of depressive episodes. In terms of the manifestation of affective disorders, depressive psychiatric disorders consist of depressive disorder and bipolar disorder.

Certain diagnostic concepts considered during the development of the classification of affective disorders are not included in the official classification system for diagnosis, although they are widely used in clinical practice. These include major depressive disorder, dysthymia, cyclothymia, mild depressive disorder, recurrent temporary depressive disorder, premenstrual dysphoric disorder, postpartum depression, post-schizophrenia depressive disorder, seasonal affective disorder, bipolar I disorder, bipolar II disorder, atypical depression, depressive stupor, rapid cycling bipolar disorder; unipolar/bipolar disorder, endogenous/reactive depression, psychotic/neurotic depression, primary/secondary depression, masked depression, dual depression, menopausal depression, retardation/agitated depression, affective disorder accompanied by physical disease, and affective disorder induced by drugs.

The physical diseases accompanying affective disorders include nervous system diseases, cardiovascular diseases (cardiomyopathy, congestive heart failure, and myocardial infarction), local or systematic tumors, infectious diseases, endocrine disorders, inflammation and vitamin deficits, etc.

To achieve the objectives of the present invention, 20(S)-protopanaxadiol can be combined with other pharmaceutically acceptable additives in preparation of a medicament.

The medicament can be used in any form known in the field, preferably a liquid oral type, an injectable type, tablets, capsules, pills or granules.

The pharmaceutically acceptable additives, which are within the knowledge of technicians working in the field, can be selected and combined according to the form required. For instance, water can be used in orally administrable forms as a solvent in combination with emulsifiers such as Tween and sweeteners such as sucrose.

The level of 20(S)-protopanaxadiol per dose can be adjusted based on the dosage of the preparation of medicament, for instance, 10 to 100 mg 20(S)-protopanaxadiol could be present in a unit dosage.

Biogenic amines are closely related to depressive psychiatric disorders. Patients with this disorder suffer from abnormalities in levels of biogenic amine and monoamine-related neural functions and structures. Norepinephrine (NE) and serotonin (5-HT) are deemed to be the most closely related with affective disorder. Hence, NE and/or 5-HT re-uptake inhibitors are the main active components of antidepressants.

As disclosed in the present invention, a series of pharmacodynamic experiments confirmed that 20(S)-protopanaxadiol has anti-depression activity.

Anti-depression animal model tests indicated that (i) in a reserpine-induced ptosis depression model using mice, a 15 mg/kg dose of 20(S)-protopanaxadiol had a remarkable inhibitory effect against ptosis induced by reserpine in a multiple dose test (ten-day course); (ii) in a reserpine-induced akinesia depression model using mice, a 15 mg/kg dose of 20(S)-protopanaxadiol had a remarkable inhibitory effect against akinesia induced by reserpine by a multiple dose test (ten-day course); (iii) in a tail suspension depression model using mice, 20(S)-protopanaxadiol remarkably decreased the tail suspension time at a dose of 15 mg/kg ($p<0.05$) in a single-dose test. In a multiple dose test (10-day course), administering to mice with 15, 7.5 and 3.75 mg/kg of 20(S)-protopanaxadiol significantly or remarkably decreased the tail suspension time; (iv) in the forced swimming depression model, administering to mice with single doses of 15, 7.5 and 3.75 mg/kg of 20(S)-protopanaxadiol significantly or remarkably decreased the duration of immobility of swimming mice within 4 minutes. With multiple-dosing (10-day course) of mice using 15, 7.5 and 3.75 mg/kg of 20(S)-protopanaxadiol, the duration of immobility in the forced swimming test decreased significantly within 4 minutes; (v) Chronic unpredictable stress testing of rats indicated that administration of 13.33 and 6.67 mg/kg doses of 20(S)-protopanaxadiol could extremely significantly or significantly increase the number of rearing of rats, and significantly or remarkably increase the number of crossing of rats; (vi) in a rat grip device depression model, test results indicated that 13.33 and 6.67 mg/kg doses of 20(S)-protopanaxadiol extremely significantly increased the number of rearing and significantly increased the number of crossing. Even a 3.33 mg/kg dose of 20(S)-protopanaxadiol remarkably increased the number of rearing. A 6.67 mg/kg dose of 20(S)-protopanaxadiol remarkably increased the level of NE in brains of model rats. A 3.33 mg/kg dose of 20(S)-protopanaxadiol remarkably increased the level of NE, 5-HT and HAV in brains of model rats.

The anti-depression pharmacological tests indicated that 15 and 7.5 mg/kg dosages of 20(S)-protopanaxadiol significantly enhanced tremors induced by 5-HTP over-stimulation and enhanced the behavioral effects of levodopa. Re-uptake of 5-HT and NA was extremely significantly, significantly or remarkably inhibited with 10, 1 and 0.1 μg/ml doses of 20(S)-protopanaxadiol respectively.

Plant-derived 20(S)-protopanaxadiol has great promise as an antidepressant because of its therapeutic efficacy and because it can be manufactured with simple techniques at low cost.

EXAMPLES

The following examples are set forth to aid in the understanding of the present invention, and should not be construed to limit in any way the scope of the invention.

Example 1

5.0 kg notoginseng folium saponins, 60 kg n-butanol and 6.0 kg ethylate sodium were put into the reactor and mixed with oxygenation to ensure constant bubbling into the bubble meter. The temperature was then raised and kept at 95±5° C. After 72 hours, the temperature was lowered to 50° C., and the reactor was washed sequentially with 70 kg and 30 kg of n-butanol-saturated water. After the water was removed, the n-butanol layer was decompressed and concentrated to dryness and the n-butanol was recycled. Then, 50 kg extractions of water were added to the residues, and mixed. The mixture was subjected to three consecutive extractions with 25 kg, 12 kg and 12 kg of acetic ether. When the water layer was removed, the acetic ether layers were combined, and the mixture was washed twice with saturated brine, 15 kg each time. The water layer was removed and 3 kg of natrii sulfas exsiccatus were added to the acetic ether layer. After torrefaction, the layer was decompressed and concentrated to dryness. The acetic ether was recycled to obtain the crude protopanaxadiol, to which 2.0 kg acetic ether were added, and mixed. This mixture was then subjected to silica gel column chromatography, and was eluted with 200 L ligroin (60~90° C.)-acetic ether (3:1) and 500 L ligroin (60~90° C.)-acetic ether (1:1) at a flow rate of 8±2 L/H. The fractions were collected in volumes of 4.0±0.5 L. The contents of each fraction were inspected by TLC and the fraction with the single component was decompressed and concentrated. The residues were dried for 16 hours in a 70° C. vacuum, and 20(S)-protopanaxadiol was thereby obtained.

Example 2

Ten grams of 20(S)-protopanaxadiol were mixed with a suitable amount of lactose. This material was processed into granules using the 70%-pure ethanol as the adhesive. Then the granules were put into capsules; each granule containing 50 mg 20(S)-protopanaxadiol.

Example 3

Ten grams of 20(S)-protopanaxadiol were added to water containing a suitable amount of emulsifier (Tween, Span, etc.), and the mixture was ground into a milky paste. Water was then added to a volume of 1,000 ml to obtain the orally administrable liquid.

Example 4

The water used in the emulsion of Example 3 was changed to a solution suitable for injection. The injection liquid was obtained after filtration, sterilization and encapsulation.

Example 5

Ten grams of 20(S)-protopanaxadiol were mixed with a suitable amount of lactose. The mixture was granulated with 70%-pure ethanol as the adhesive. After torrefaction, Magnesium Stearate was added and the material compressed into tablets, each of which contained 50 mg 20(S)-protopanaxadiol.

Example 6

Ten grams of 20(S)-protopanaxadiol were mixed with a suitable amount of sucrose. The mixture was made into granules with 70%-pure ethanol as the adhesive. Then, granules were produced after torrefaction.

Trial Example 1

Typical trial models to substantiate anti-depression activity are used to study the pharmacodynamics of the present invention.

1. Inhibition of Reserpine-Induced Ptosis
(1) Test Substance
   (i) Drugs

The 20(S)-protopanaxadiol used was manufactured by Shanghai Innovative Research Center of Traditional Chinese Medicine (SIRC/TCM), Lot No.: 050501, purity: 93.62%. Dosage and direction: for clinical practice, daily oral administration of 50 mg to adults weighing 60 kg; the daily adult dosage was calculated as follows: 50 mg/24 h÷60 kg (weight)=0.83 mg/kg (weight). Preparation for trial: 20(S)-protopanaxadiol was made as a suspension by transonic mixing with 0.3% CMCNa/Tween-80 solution.

Fluoxetine was from Lilly, USA, 20 mg/pill, Lot No.: A103400, was adjusted to the desired concentration with 0.3% CMCNa solution before use.

Injectable Reserpine was obtained from Bangmin (Guangdong) Pharmaceutical Factory, 1 mg/ml, Lot No.: 050411.

The 0.3% CMCNa/Tween-80 solution was mixed at a volume ratio of 200:1.

TABLE 1

20(S)-protopanaxadiol Dosage Design

| Animals | Groups | Reagents | Concentration (mg/ml) | Volume (ml/kg) | Dose (mg/kg) | Total doses given | Administration route |
|---|---|---|---|---|---|---|---|
| Mice | Solvent control | 0.3% CMCNa + Tween-80 | — | — | — | — | i.g |
|  | Model control | 0.3% CMCNa + Tween-80 | — | — | — | — | i.g |
|  | Fluoxetine group | Fluoxetine | 1.8 | 10 | 18 | 18 | i.g |
|  | Estazolam group | Estazolam | 0.06 | 10 | 0.6 | 18 | i.g |
|  | High-dose group | 20(S)-protopanaxadiol | 1.5 | 10 | 15 | 18 | i.g |
|  | Medium-dose group | 20(S)-protopanaxadiol | 0.75 | 10 | 7.5 | 9 | i.g |
|  | Low-dose group | 20(S)-protopanaxadiol | 0.375 | 10 | 3.75 | 4.5 | i.g |
| Rats | Solvent control | 0.3% CMCNa + Tween-80 | — | 10 | — | — | i.g |
|  | Model control | 0.3% CMCNa + Tween-80 | — | 10 | — | — | i.g |
|  | Fluoxetine group | Fluoxetine | 1.6 | 10 | 16 | 16 | i.g |

TABLE 1-continued

20(S)-protopanaxadiol Dosage Design

| Animals | Groups | Reagents | Concentration (mg/ml) | Volume (ml/kg) | Dose (mg/kg) | Total doses given | Administration route |
|---|---|---|---|---|---|---|---|
| | High-dose group | 20(S)-protopanaxadiol | 1.33 | 10 | 13.33 | 16 | i.g |
| | Medium-dose group | 20(S)-protopanaxadiol | 0.67 | 10 | 6.67 | 8 | i.g |
| | Low-dose group | 20(S)-protopanaxadiol | 0.33 | 10 | 3.33 | 4 | i.g |

Note:
The solvent control group was without modeling, the model control was with modeling.

(ii) Test Animals

Kunming mice, Production License No.: SCXK (Chuan) 2003-06.

(2) Methods and Results

Fifty male Kunming mice, 8-9 weeks old and weighing 18-22 g, were randomly divided by weight into 5 groups, and administered by gavage a single dose of one of the drugs listed in Table 3 for 10 consecutive days. Sixty minutes after the last dose, mice were given an i.p. injection of reserpine (2 mg/kg). After 60 minutes, mice were put on a bracketed stand and observed for 2 minutes. The number of animals with at least one upper eyelid closed was recorded. Fisher's exact test was used for statistical analysis. Results were shown in Table 2.

TABLE 2

Inhibition Effects of 20(S)-protopanaxadiol on Reserpine-Induced Ptosis in Mice

| Test groups | Dose × times (mg/kg × T) | Number of animals | Number of animals with at least one upper eyelid closed |
|---|---|---|---|
| Model | — | 10 | 10 |
| Fluoxetine | 18 × 10 | 10 | 4* |
| High-dose 20(S)-protopanaxadiol | 15 × 10 | 10 | 5* |
| Medium-dose 20(S)-protopanaxadiol | 7.5 × 10 | 10 | 8 |
| Low-dose 20(S)-protopanaxadiol | 3.75 × 10 | 10 | 9 |

Note:
the dosed groups compared with the model group: *p < 0.05.

As shown in Table 2, at a dose of 15 mg/kg, 20(S)-protopanaxadiol had a remarkable inhibitory effect on ptosis induced in mice by reserpine in the multiple dose test (*p<0.05).

2. Inhibition of Akinesia Induced by Reserpine (1) Test Substance (i) Drugs

20(S)-protopanaxadiol, fluoxetine and injectable reserpine (see Section 1. (1) (i)).

(ii) Test Animals

Kunming mice, Production License No.: SCXK (Chuan) 2003-06.

(2) Methods and Results

Fifty male Kunming mice, 8-9 weeks old and weighing 18-22 g, were randomly divided by weight into 5 groups, and administered by gavage a single dose of one of the drugs listed in Table 5 for 10 consecutive days. Sixty minutes after the last dose, mice were given a reserpine injection (2.5 mg/kg) delivered i. p. Sixty minutes later, mice were individually placed on the center of a round filter paper 7.5 cm in diameter. After a 30-sec observation, the number of animals that were still on the filter paper was recorded. Fisher's exact test was used for statistical analysis. Results were shown in Table 3.

TABLE 3

Inhibition Effects of Multiple Dose of 20(S)-protopanaxadiol on Reserpine-Induced Akinesia in Mice

| Test groups | Dose × times (mg/kg × T) | Number of animals | Number of animals Remaining on the filter paper for 30 seconds |
|---|---|---|---|
| Model | — | 10 | 10 |
| Fluoxetine | 18 × 10 | 10 | 3** |
| High-dose 20(S)-protopanaxadiol | 15 × 10 | 10 | 5* |
| Medium-dose 20(S)-protopanaxadiol | 7.5 × 10 | 10 | 7 |
| Low-dose 20(S)-protopanaxadiol | 3.75 × 10 | 10 | 8 |

Note:
dosed groups compared with the model group: *p < 0.05, **P < 0.01.

As shown in Table 3, a dose of 15 mg/kg of 20(S)-protopanaxadiol had a remarkable inhibitory effect on akinesia induced in mice by reserpine in the multiple dose test (p<0.05).

3. Tail Suspension Test in Mice (1) Test Substances (i) Drugs

20(S)-protopanaxadiol and fluoxetine (see Section 1. (1) (i)).

(ii) Test Animals

Kunming mice, Production License No.: SCXK (Chuan) 2003-06.

(2) Methods and Results (i) Effects on Mice of a Single Dose of 20(S)-protopanaxadiol in the Tail Suspension Test Fifty male Kunming mice, 9-10 weeks old and weighing 22-24 g, were randomly divided by weight into 5 groups and administered by gavage a dose of one of the drugs listed in Table 6. Sixty minutes later, mice were individually suspended by the tail (1 cm from the tip) to a horizontal 1 cm-diameter PVC bar by use of the adhesive tape. The tail of mouse was thereby prevented from twisting. The PVC bar was placed overhead to suspend the mouse upside-down, keeping the head 5 cm above the table surface. To avoid interference, each mouse was partitioned by clapboard. The duration of immobility of each animal within a 6-min period was recorded (the term immobility indicates that mice did not move except for respiration). T-test was used for statistical analysis. Results were shown in Table 4.

TABLE 4

Effects on Mice of a Single Dose of 20(S)-protopanaxadiol in the Tail Suspension Test

| Test groups | Dose × times (mg/kg × T) | Number of animals | Cumulative immobility within 6 minutes (sec, x ± SD) |
|---|---|---|---|
| Model | — | 10 | 108.40 ± 27.45 |
| Fluoxetine | 18 × 1 | 10 | 70.90 ± 23.11** |
| High-dose 20(S)-protopanaxadiol | 15 × 1 | 10 | 85.40 ± 20.21* |
| Medium-dose 20(S)-protopanaxadiol | 7.5 × 1 | 10 | 92.30 ± 32.93 |
| Low-dose 20(S)-protopanaxadiol | 3.75 × 1 | 10 | 95.00 ± 36.21 |

Note:
the dosed groups compared with the model group: *p < 0.05, **P < 0.01.

As shown in Table 4, 20(S)-protopanaxadiol remarkably decreased the tail suspension time at a dose of 15 mg/kg (p<0.05) in the single-dose test.

(ii) Effects on Mice of Multiple Doses of 20(S)-protopanaxadiol in the Tail Suspension Test Fifty male Kunming mice, 8-9 weeks old and weighing 18-22 g, were randomly divided by weight into 5 groups, and administered by gavage a dose of one of the drugs listed in Table 7 for 10 consecutive days. Sixty minutes after the last dose, mice were individually suspended by the tail (1 cm from the tip) from a horizontal 1 cm-diameter PVC bar using the adhesive tape. The tail of the mouse was thereby prevented from twisting. The PVC bar was placed overhead to suspend the mouse upside down, keeping the head 5 cm above the table surface. To avoid interference, each mouse was partitioned by clapboard. The duration of immobility of each animal within a 6-min period was recorded (the term immobility indicates that the mice did not move except for respiration). Results were shown in Table 5.

TABLE 5

Effects on Mice of Multiple Dose of 20(S)-protopanaxadiol in the Tail Suspension Test

| Test groups | Dose × times (mg/kg × T) | Number of animals | Cumulative immobility within 6 minutes (sec, x ± SD) |
|---|---|---|---|
| Model | — | 10 | 111.60 ± 21.93 |
| Fluoxetine | 18 × 10 | 10 | 59.10 ± 35.40*** |
| High-dose 20(S)-protopanaxadiol | 15 × 10 | 10 | 69.90 ± 25.71** |
| Medium-dose 20(S)-protopanaxadiol | 7.5 × 10 | 10 | 73.90 ± 37.53* |
| Low-dose 20(S)-protopanaxadiol | 3.75 × 10 | 10 | 83.60 ± 35.52* |

Note:
dosed groups compared with the model group: *p < 0.05, P < 0.01, *P < 0.001.

As shown in Table 5, at doses of 15, 7.5 and 3.75 mg/kg in the multiple-dose test, 20(S)-protopanaxadiol could significantly or remarkably decreased the tail suspension time (P<0.01, P<0.05).

4. Forced Swimming Test Using Mice (1) Test Substances (i) Drugs

20(S)-protopanaxadiol, fluoxetine and reserpine injection (see Section 1. (1) (i)).

(ii) Test Animals

Kunming mice, male, Production License No.: SCXK (Chuan) 2003-06.

(2) Methods and Results (i) Effects on Mice of a Single Dose of 20(S)-protopanaxadiol in the Forced Swimming Test Fifty male Kunming mice, 9-10 weeks old and weighing 22-24 g, were randomly divided by weight into 5 groups and administered by gavage a single dose of one of the drugs listed in Table 6. Sixty minutes later, the mice were placed in individual beakers (2500 ml, 20 cm×14 cm in diameter), which had previously been filled with water (25° C.) up to 10 cm from the bottom. The duration of immobility in the last 4 minutes in the 6-min swimming test was recorded (the term immobility indicates no movement except for respiration). T-test was used for statistical analysis. Results were shown in Table 6.

TABLE 6

Effects on Mice of a Single Dose of 20(S)-protopanaxadiol in the Forced Swimming Test

| Test Groups | Dose × times (mg/kg × T) | Number of animals | Cumulative immobility within 6 minutes (sec, x ± SD) |
|---|---|---|---|
| Model | — | 10 | 131.80 ± 40.67 |
| Fluoxetine | 18 × 1 | 10 | 86.20 ± 32.56* |
| High-dose 20(S)-protopanaxadiol | 15 × 1 | 10 | 86.60 ± 33.09** |
| Medium-dose 20(S)-protopanaxadiol | 7.5 × 1 | 10 | 88.10 ± 24.84** |
| Low-dose 20(S)-protopanaxadiol | 3.75 × 1 | 10 | 97.00 ± 30.96* |

Note:
dosed groups compared with the model group: *p < 0.05, **P < 0.01.

As shown in Table 6, a single dose of 15 and 7.5 mg/kg (p<0.01) as well as 3.75 mg/kg (p<0.05) 20(S)-protopanaxadiol significantly or remarkably decreased the duration of immobility of swimming mice within 4 minutes.

(ii) Effects on Mice of Multiple Doses of 20(S)-protopanaxadiol in the Forced Swimming Test Fifty male Kunming mice, 8-9 weeks old and weighing 18-22 g, were randomly divided by weight into 5 groups and subjected to gavage once a day for 10 consecutive days as shown in Table 7. Sixty minutes after the last dose, the mice were individually placed in beakers (2500 ml, 20 cm×14 cm in diameter), which had previously been filled with water (25° C.) up to 10 cm from the bottom. The cumulative time of immobility in the last 4 minutes of a total swimming time of 6 minutes was recorded (the term immobility indicates no movement except for respiration). T-test was used for statistical analysis. Results were shown in Table 7.

TABLE 7

Effects on Mice of Multiple Doses of 20(S)-protopanaxadiol in the Forced Swimming Test

| Test Groups | Dose × times (mg/kg × T) | Number of animals | Cumulative immobility within 4 minutes (sec, mean ± SD) |
|---|---|---|---|
| Model | — | 10 | 140.50 ± 50.15 |
| Fluoxetine | 18 × 10 | 10 | 81.50 ± 36.77** |
| High-dose 20(S)-protopanaxadiol | 15 × 10 | 10 | 71.30 ± 32.53** |
| Medium-dose 20(S)-protopanaxadiol | 7.5 × 10 | 10 | 79.30 ± 33.70** |
| Low-dose 20(S)-protopanaxadiol | 3.75 × 10 | 10 | 84.00 ± 32.60** |

Note:
dosed groups compared with the model group: **P < 0.01.

As shown in Table 7, at multiple doses of 15, 7.5 and 3.75 mg/kg, 20(S)-protopanaxadiol significantly decreased the duration of immobility of mice in the forced swimming test within 4 minutes (p<0.01).

5. Chronic Unpredictable Stress Testing of Rats (1) Test Substances (i) Drugs

20(S)-protopanaxadiol and fluoxetine (see Section 1. (1) (i)).

(ii) Test Animals

SD rats, male, Production License No.: SCXK (Chuan) 2003-06.

(2) Methods and Results

Male stressed SD rats were housed individually and exposed for 21 days to the following unpredictable stressors: ice water swimming (4° C., 5 min), tail pinch (3 min), water deprivation (40 h), food deprivation (40 h), paired feeding, wet bedding, binding, and overnight lighting, each stress was applied two or three times. Animals in the non-stressed control group were housed 5 per cage. At the same time, animals were administered drugs by gavage for 21 consecutive days as shown in Table 8. An open-field test was used to observe behavior. A large cubiform box (80×80×40 cm) was employed in which the floor was divided into 25 grids of equal size using white lines, with the same size grids also marked on the surrounding walls. The number of floor grids crossed (crossing) and the number of rearing up on hind limbs (rearing) were recorded. Observations of each rat were made every 3 minutes on the 22nd day. T test was used for statistical analysis. Results were shown in Table 8.

3,4-Dihydroxyphenylacetic acid (DOPAC) was from Fluka, 1 g/bottle, purity: 98%, EC No.: 2030241, Lot & Filling Code: 48256/3 42932;

3,4-Dihydroxybenzylamine hydrobromide acid (DHBA) was from Fluka, 250 mg/bottle, purity: $\geq$98%, EC No.: 2403828, Lot & Filling Code: 311612/1 52832;

Serotonin hydrochloride (5-HT) was from Fluka, 100 mg/bottle, purity: $\geq$98%, EC No.: 2444644, Lot & Filling Code: 357345/140808;

5-Hydroxy-3-indoleacetic acid (5-HIAA) was from Fluka, 250 mg/bottle, purity: $\geq$99%, EC No.: 2001954, Lot & Filling Code: 403262/1 22708;

Homovanillic acid (HVA) was from Fluka, 250 mg/bottle, purity: $\geq$99%, EC No.: 2061767, Lot & Filling Code: 417865/162609;

Noradrenalini Bitartras (NA) was from National Institute for the Control of Pharmaceutical and Biological Products, purity: $\geq$98%, 100 mg/bottle, Lot No.: 169-9402;

Adrenaline (Adr) was from the National Institute for the Control of Pharmaceutical and Biological Products, purity: $\geq$98%, 50 mg/bottle, Lot No.: 0154-9402.

(iii) Instruments

HPLC LC-10AT equipped with an L-ECD-6A electrochemical detector, Shimadzu, Japan; N2000 Chromatography Work Station (Intelligence Information Institute, Zhejiang University)

(iv) Test Animals

SD rats, Production License No.: SCXK (Chuan) 2003-06

(2) Methods and Results

TABLE 8

Effects on Rats of 20(S)-protopanaxadiol in the Open-field Chronic Stress Test

| Test Groups | Dose × times (mg/kg × T) | Number of animals | Number of crossing (times/3 min, mean ± SD) | Number of rearing (times/3 min, mean ± SD) |
|---|---|---|---|---|
| Control | — | 10 | 55.70 ± 16.32 | 11.30 ± 3.37 |
| Model | — | 10 | 22.60 ± 10.45ΔΔΔ | 4.40 ± 2.12ΔΔΔ |
| Fluoxetine | 16 × 21 | 10 | 44.40 ± 1.45*** | 11.30 ± 3.43*** |
| High-dose 20(S)-protopanaxadiol | 13.33 × 21 | 10 | 40.80 ± 12.93** | 9.50 ± 3.34*** |
| Medium-dose 20(S)-protopanaxadiol | 6.67 × 21 | 10 | 38.60 ± 21.14* | 8.90 ± 4.18** |
| Low-dose 20(S)-protopanaxadiol | 3.33 × 21 | 10 | 32.90 ± 13.19 | 6.50 ± 2.64 |

Note:
(i) the model group compared with the control group: ***p < 0.001;
(ii) dosed group compared with the model group: *p < 0.05, p < 0.01, *p < 0.001.

As shown in Table 8, the number of rearing and crossing of model rats were extremely significantly decreased (p<0.001), demonstrating the validity of the trial model used. Compared with the model group, the number of rearing of rats in the groups treated with 20(S)-protopanaxadiol at 13.33 and 6.67 mg/kg doses were extremely significantly or significantly increased (p<0.001, p<0.01). The number of crossing was also be significantly or remarkably increased at these doses (p<0.01, p<0.05).

6. Stress Testing of Rats Wearing Shackles (1) Test Substances (i) Drugs

20(S)-protopanaxadiol and fluoxetine (see Section 1. (1) (i)).

(ii) Reagents

Perchloric acid was from Dongfang (Tianjin) Chemical Factory, Lot No.: 050617;

Na2EDTA was from Xilong (Shantou) Chemical Factory, Lot No.: 040204;

(i) Modeling Method: Sixty male SD rats, 8-9 weeks old and weighing 200-250 g, were randomly divided into 6 groups and subjected to gavage once a day as shown in Table 9. On the first day, individually housed rats were fitted with a cylindrical plastic shackle-like device composed of two pieces of red organic glass 0.2 cm-thick and 4 cm in diameter. The device could be adjusted according to the size of the animals and was worn for 21 days.

(ii) Test Indexes: Behavior such as rearing up; grabbing and gnawing; braying; slowness in reactions; action tardiness; narrowing of the eyes with secretion; yellow of fur; small, dry and fewer feces; borrow-reddish fail with scales and weight loss. An open-field test was used to observe the behavior of animals on day 21 (the same method used with the chronic stress rat model). Results were shown in Table 9.

(iii) Measure of Cerebral Neurotransmitters

Preparation of Cerebral Tissues: Rats were Sacrificed by Femoral Arterial Exsanguination, and whole brains were weighed after the cerebellum was excised and homogenized in 950 μl (0.1 mol/L) perchloric acid (containing 0.05%

Na2EDTA) and 50 μl (2 μg/ml) of DHBA. This material was then centrifuged at 11,000 rpm/for 10 minutes and, 10 μl of the supernatant were taken for testing. Results were as follows: The amount of each neurotransmitter was shown as the wet weight (ng/g) in cerebral tissues.

Chromatographic conditions: Chromatography was performed with a Shimadzu HPLC system, which was equipped with an L-BCD-6A electrochemical detector (detection range: 0.1-500 nA), a chromatographic column of 5 μm, 200 mm×4.6 mm ID glassy carbon electrode; the flow rate employed was 1.2 ml/min, the operating voltage was +0.75 V; and oxygenation was maintained. An NP2000 workstation was used for data recording and processing (Intelligence Information Institute of Zhejiang University). The potential difference between the working electrode and reference electrode was 0.75 V. The mobile phase, prepared with deionized water and degassed, consisted of 0.1 mmol/L citric acid-0.1 mmol/L sodium acetate buffer at pH4.37 with 10% ethanol. A mixture of a B81.2 mmol/L ion pair and 1.3 mmol/L Di-n-butylamine was used after degasification of the G4 glass filler.

Preparation of standard solutions: The stock solutions were 2 μg/ml for DHBA and 20 μg/ml for NE, DA, DOPAC, 5-HT, 5-HIAA and HAV. Standard solution 6 was prepared by mixing 20 μl each of NE, DA, DOPAC, 5-HT, 5-HIAA and HAV, then 80 μl of 0.1 mM mmol/LHCLO4 were added. Standard solution 7 (100 ng/ml) was prepared by mixing 50 μl of standard solution 6, 50 μl DHBA and 900 μl 0.1 mmol/LHCLO4. Standard solution 7 (10 μl) was used for HPLC.

Calculation:

$$\frac{\text{sample neurotransmitter}/DHBA}{\text{standard neurotransmitter}/DHBA} \times \text{amount of standard} \times \frac{1 \text{ ml}(0.1 \text{ mmol}/LHCLO_4)}{\text{sample volume of sample}} \Big/ \text{weight of tissue (g)}$$

Results were shown in Table 10.

TABLE 9

Effects of 20(S)-protopanaxadiol on Open-field Behavior of Model Rats

| Test Groups | Dose × times (mg/kg × T) | Number of animals | Number of crossing (times/3 min, mean ± SD) | Number of rearing (times/3 min, mean ± SD) |
|---|---|---|---|---|
| Control | — | 10 | 12.90 ± 2.92 | 60.00 ± 13.96 |
| Model | — | 10 | 4.60 ± 1.84ΔΔΔ | 27.60 ± 11.34ΔΔΔ |
| Fluoxetine | 16 × 21 | 10 | 11.20 ± 3.08*** | 49.80 ± 20.31** |
| High-dose 20(S)-protopanaxadiol | 13.33 × 21 | 10 | 10.10 ± 2.60*** | 46.20 ± 10.58** |
| Medium-dose 20(S)-protopanaxadiol | 6.67 × 21 | 10 | 9.30 ± 2.00*** | 44.10 ± 13.30** |
| Low-dose 20(S)-protopanaxadiol | 3.33 × 21 | 10 | 7.00 ± 2.05* | 36.20 ± 14.26 |

Note:
(1) the model group compared with the control group: ΔΔΔp < 0.001;
(2) dosed groups compared with the model group: *p < 0.05, p < 0.01, *p < 0.001.

As shown in Table 9, the number of rearing and crossing of rats from the model group were significantly decreased (p<0.001), demonstrating the validity of the trial model used. Compared with the model group, the number of rearing (P<0.001) and crossing of rats (p<0.01) in the groups given the 13.33 and 6.67 mg/kg doses were extremely significantly or significantly increased. With the 3.33 mg/kg dose, 20(S)-protopanaxadiol noticeably increased the number of rearing (p<0.05).

TABLE 10

Effects of 20(S)-protopanaxadiol on the Concentration of Monoamine Neurotransmitter and Its Metabolite in Rats (x ± SD)

| Test Groups | Dose × times (mg/kg × T) | Concentration of monoamine neurotransmitter and its metabolite (ng/g nerve tissues) | | | | | |
|---|---|---|---|---|---|---|---|
| | | DA | DOPAC | NE | 5-HT | 5-HIAA | HAV |
| Control | — | 386.71 ± 87.00 | 22.94 ± 2.26 | 13.24 ± 2.05 | 147.94 ± 39.93 | 12.36 ± 2.95 | 58.51 ± 9.33 |
| Model | — | 377.40 ± 39.41 | 20.52Δ ± 2.31 | 10.30ΔΔ ± 1.77 | 99.98ΔΔ ± 14.95 | 8.13Δ ± 1.11 | 47.84Δ ± 8.09 |
| Fluoxetine | 16 × 21 | 406.97 ± 49.91 | 21.53 ± 3.15 | 13.67*** ± 0.91 | 136.88*** ± 14.49 | 8.42 ± 1.16 | 62.17*** ± 4.34 |
| High-dose 20(S)-protopanaxadiol | 13.33 × 21 | 394.41 ± 50.27 | 20.68 ± 3.36 | 11.04 ± 1.49 | 102.81 ± 12.56 | 8.62 ± 1.52 | 53.19 ± 8.76 |

TABLE 10-continued

Effects of 20(S)-protopanaxadiol on the Concentration of Monoamine Neurotransmitter and Its Metabolite in Rats (x ± SD)

| Test Groups | Dose × times (mg/kg × T) | Concentration of monoamine neurotransmitter and its metabolite (ng/g nerve tissues) | | | | | |
|---|---|---|---|---|---|---|---|
| | | DA | DOPAC | NE | 5-HT | 5-HIAA | HAV |
| Medium-dose 20(S)-protopanaxadiol | 6.67 × 21 | 401.67 ± 34.93 | 22.17 ± 2.83 | 12.13* ± 1.67 | 113.18 ± 18.12 | 9.02 ± 2.33 | 56.37 ± 10.80 |
| Low-dose 20(S)-protopanaxadiol | 3.33 × 21 | 375.96 ± 32.11 | 21.57 ± 2.35 | 12.15* ± 1.31 | 114.98* ± 13.50 | 8.78 ± 1.75 | 57.30* ± 7.50 |

Note:
(1) the model group compared with the control group:
Δp < 0.05,
ΔΔp < 0.01;
(2) dosed groups compared with the model group:
*p < 0.05,
***p < 0.001.

As shown in Table 10, the levels of DOPAC, 5-HIAA, HAV, NE and 5-HT were remarkably or significantly decreased in the model group compared with the control group (p<0.05, p<0.01), demonstrating the validity of the trial model used. The level of NE was remarkably increased in rats administered 20(S)-protopanaxadiol at a dose of 6.67 mg/kg for 21 consecutive days (p<0.05). The levels of NE, 5-HT and HAV were remarkably increased in rats administered 20(S)-protopanaxadiol at a dose of 3.33 mg/kg for 21 consecutive days (p<0.05).

7. Analysis of Anti-depression Pharmacological Effects 7.1 L-5-HTP Induced Tremor Testing of Mice (1) Test Substances (i) Drugs 20(S)-protopanaxadiol and fluoxetine (see Section 1. (1) (i)).

L-5-HTP, Sigma, Lot No.: 112K1258.

(ii) Test Animals

Kunming male mice, Production License No.: SCXK (Chuan) 2003-06.

(2) Methods and Results

Seventy male Kunming mice, 8-9 weeks old and weighing 18-22 g, were randomly divided by weight into 7 groups and administered a single dose by gavage as shown in Table 13. Sixty minutes later, mice received an i.p. injection of 5-HTP at a dose of 200 mg/kg (the maximal dose at which tremors were not induced). Then, mice were individually put into cages (16×27 cm) and observed for 20 minutes. The number of animals with tremors was recorded. Fisher's exact test was used for statistical analysis. Results were shown in Table 11.

TABLE 11

Effects of 20(S)-protopanaxadiol on 5-HTP-Induced Tremors in Mice

| Test Groups | Dose × times (mg/kg × T) | Number of animals | Number of running animals |
|---|---|---|---|
| 0.3% CMCNa+ Tween-80 solution + 5-HTP | — | 10 | 0 |
| Fluoxetine | 18 × 1 | 10 | 0 |
| Fluoxetine group (with 5-HTP) | 18 × 1 | 10 | 8*** |
| 20(S)-protopanaxadiol | 15 × 1 | 10 | 0 |
| 20(S)-protopanaxadiol(with 5-HTP) | 15 × 1 | 10 | 6* |
| 20(S)-protopanaxadiol (with 5-HTP) | 7.5 × 1 | 10 | 5* |
| 20(S)-protopanaxadiol(with 5-HTP) | 3.75 × 1 | 10 | 2 |

Note:
dosed groups compared with the 0.3% CMCNa+ Tween-80 solution + 5-HTTP group: *p < 0.05, **p < 0.001.

As shown in Table 11, tremors were not observed in any animal administered L-5-HTP or 20(S)-protopanaxadiol only. When rats were given 20(S)-protopanaxadiol, followed by 5-HTP, more animals with tremor were observed, along with the increase of dosage. At doses of 15 and 7.5 mg/kg (p<0.05), 20(S)-protopanaxadiol remarkably enhanced tremors induced by 5-HTP.

7.2 Enhancement of the Behavioral Effects of Levodopa on Mice (1) Test Substances (i) Drugs 20(S)-protopanaxadiol and fluoxetine (see Section 1. (1) (i)).

Levodopa was from Shuguang (Beijing) Pharmaceutical Co. Ltd, Lot No.: 041120, 25 g×100 tablets, and was prepared as a 20 mg/ml solution by adding distilled water. After centrifugation at the 2500 rpm/min rate for 20 minutes, the supernatant was removed and stored.

(ii) Test Animals

Kunming mice, Production License No.: SCXK (Chuan) 2003-06.

(2) Methods and Results

Seventy male Kunming mice, 8-9 weeks old and weighing 18-22 g, were randomly divided by weight and sex into 7 groups and administered a single dose by gavage as shown in Table 14. Sixty minutes later, levodopa at a dose of 200 mg/kg (the maximal dose not inducing running in mice) was administered i. p. Then, mice were put into separate cages and observed for 30 minutes. The number of running mice was recorded. Fisher's exact test was used for statistical analysis. Results were shown in Table 12.

TABLE 12

Effects of 20(S)-protopanaxadiol on Levodopa Behavior in Mice

| Test Groups | Dose × times (mg/kg × T) | Number of animals | Number of running animals |
|---|---|---|---|
| 0.3% CMCNa+ Tween-80 SOLUTION (with levodopa) | — | 10 | 0 |
| Fluoxetine (without levodopa) | 18 × 1 | 10 | 0 |
| Fluoxetine (with levodopa) | 18 × 1 | 10 | 7** |
| 20(S)-protopanaxadiol (without levodopa) | 15 × 1 | 10 | 0 |

TABLE 12-continued

Effects of 20(S)-protopanaxadiol on Levodopa Behavior in Mice

| Test Groups | Dose × times (mg/kg × T) | Number of animals | Number of running animals |
|---|---|---|---|
| 20(S)-protopanaxadiol (with levodopa) | 15 × 1 | 10 | 5* |
| 20(S)-protopanaxadiol (with levodopa) | 7.5 × 1 | 10 | 5* |
| 20(S)-protopanaxadiol (with levodopa) | 3.75 × 1 | 10 | 2 |

Note:
dosed groups compared with the 0.3% CMCNa+Tween-80 solution (with LEVODOPA) group: *p < 0.05, **p < 0.01.

As shown in Table 12, tremors were not observed in animals administered only levodopa or 20(S)-protopanaxadiol. When mice were given 20(S)-protopanaxadiol, followed by levodopa, more animals with behavioral effects were observed, along with the increase of dosage. At doses of 15 and 7.5 mg/kg (p<0.05), 20(S)-protopanaxadiol remarkably enhanced behavioral effect of levodopa.

7.3 5-HT Re-uptake Test
(1) Test Substances
    (i) Drugs
    20(S)-protopanaxadiol, manufactured by Shanghai Innovative Research Center of Traditional Chinese Medicine, Lot No.: 050501, purity: 93.62%. Preparation: 20(S)-protopanaxadiol was transonicly mixed to obtain the required concentration by adding sodium chloride injection at the 0.9% concentration.
    Fluoxetine, Lilly, USA, 20 mg/pill, Lot No.: A103400, was transonicly mixed to obtain for the required concentration by adding sodium chloride injection at a 0.9% concentration.
    0.9% sodium chloride injection: Kelun (Sichuan) Pharmaceutical Co. Ltd., 500 ml/bottle, Lot No.: B050925.
    (ii) Reagents
    NaHCO3: Dongshi (Chongqing) Chemical Factory Co. Ltd., Lot No.: 20030624
    Na2CO3, Kelong (Chengdu) Chemical Reagent Factory, Lot No.: 20050811
    [14C]-5-HT: DuPont, USA, 250 μCi/bottle, Lot No.: 3167243, ratio radio-activity: 3.7 MBq/ml
    (iii) Instruments
    1s60000IC scintillation counter, Beckman
    (iv) Test Animals
    SD rats, Production License No.: SCXK (Chuan) 2003-06.
(2) Methods and Results
Eight male SD rats were decapitated. The hypothalamuses were rapidly removed, weighed and homogenized in a 9-fold volume of 0.32 mol/L ice-cold sucrose solution, and centrifuged at a rate of 3420 rpm for 10 minutes at 0-4° C. Then, 200 μl of supernatant were mixed with 800 μl [$^{14}$C]-5-HT at a concentration of 62.5 nmol/L (prepared with NaHCO3/Na2CO3 buffer solution), and 20 μl 20(S)-protopanaxadiol solution (20 μl of 0.9% NaCl injection were added for the control group). Ten tubes were prepared for each group and all tubes were incubated at 37° C. for 5 minutes. An additional tube was used to homogenize 200 μl of the supernatant, 800 μl [$^{14}$C]-5-HT at a concentration of 62.5 nmol/L (prepared with NaHCO3/Na2CO3 buffer solution) and 20 μl of 0.9% NaCl injection and was incubated in a 0° C. $CO_2$ chamber for 5 minutes, followed by centrifugation at a rate of 7,480 rpm for 10 minutes. The supernatant of the solution was put into a scintillation vial for counting after adding 10 ml scintillation fluid (scintillation was performed 3 times). The re-uptake of serotonin was calculated by the difference in DMP at 37° C. and 0° C.

$$\text{Inhibition rate} = \frac{\text{mean re-uptake of the control group} - \text{mean re-uptake of the dosed group}}{\text{mean re-uptake of the control group}} \times 100\%$$

TABLE 13

Effects of 20(S)-protopanaxadiol on 5-HT Re-uptake

| Test groups | Concentration (μg/ml) | Number of samples | Amount of re-uptake (dmp) | Inhibitory rate (%) |
|---|---|---|---|---|
| Control | — | 10 | 4959.7 ± 877.1 | — |
| Fluoxetine | 1 | 10 | 3286.9 ± 526.2*** | 33.7 |
| 20(S)-protopanaxadiol | 10 | 10 | 3696.4 ± 392.9*** | 25.5 |
| 20(S)-protopanaxadiol | 1 | 10 | 3963.5 ± 459.4** | 20.1 |
| 20(S)-protopanaxadiol | 0.1 | 10 | 4117.3 ± 532.0* | 17.0 |
| 20(S)-protopanaxadiol | 0.01 | 10 | 4377.8 ± 479.7 | 11.7 |

Note:
dosed groups compared with the control group: *p < 0.05, p < 0.01 *p < 0.001.

As shown in Table 13, 20(S)-protopanaxadiol at a concentration of 10, 1 or 0.1 μg/ml could extremely significantly, significantly and remarkably inhibit the re-uptake of 5-HT (P<0.05, P<0.01, P<0.001). The inhibitory rates were 25.5%, 20.1% and 17.0%, respectively.

7.4 NA Re-uptake Test
(1) Test Substances
    (i) Drugs
    20(S)-protopanaxadiol, fluoxetine and 0.9% NaCl injection (see Section 7.3 (1) (i)).
    (ii) Reagents
    NaHCO3: Dongshi (Chongqing) Chemical Factory Co. Ltd., Lot No.: 20030624
    Na2CO3: Kelong (Chengdu) Chemical Reagent Factory, Lot No.: 20050811
    [3H]-norepinephrine: DuPont, USA, 250 Ci/bottle, Lot No.: 3242681, ratio radio-activity: 3.7 Bq/ml.
    (iii) Instruments
    1s60000IC scintillation counter, Beckman
    (iv) Test Animals
    SD rats, Production License No.: SCXK (Chuan) 2003-06.
(2) Methods and Results
Male SD rats were sacrificed by decapitation. The corpus striatum was rapidly removed, weighed and homogenized in a 9-fold volume of 0.32 mol/L ice-cold sucrose, and centrifuged at a rate of 3,420 rpm, 0-4° C. for 10 minutes. Then, 200 μl of supernatant were mixed with 800 μl [$^{3}$H]-norepinephrine at a concentration of 62.5 nmol/L (prepared with NaHCO3/Na2CO3 buffer solution) and 20 μl 20(S)-protopanaxadiol solution (20 μl 0.9% NaCl injection was used instead for the control group). Ten tubes were prepared for each group and incubated in the CO2 chamber at 37° C. for 5 minutes. An additional tube was used to homogenize 200 μl supernatant, 800 μl [3H]-NA at a concentration of 62.5 mol/L (prepared with NaHCO3/Na2CO3 buffer solution) and 20 μl 0.9% NaCl injection, and was then incubated in the 0° C. CO2 chamber for 5 minutes, followed by centrifugation at a rate of 7,480 rpm for 10 minutes. The supernatant of the solution was put into the scintillation vial for counting after adding 10 ml of scintillation fluid (scintillation was performed 3 times). The re-uptake of serotonin was calculated by the difference in DMP at 37° C. and 0° C.:

$$\text{Inhibition rate} = \frac{\text{mean re-uptake of the control group} - \text{mean re-uptake of the dosed group}}{\text{mean re-uptake of the control group}} \times 100\%$$

TABLE 14

Effects of 20(S)-protopanaxadiol on NA Re-uptake

| Test groups | Concentration (μg/ml) | Number of samples | Amount of re-uptake (dmp) | Inhibitory rate (%) |
|---|---|---|---|---|
| Control | — | 10 | 5593.7 ± 190.0 | — |
| Fluoxetine | 1 | 10 | 4311.8 ± 733.8*** | 22.9 |
| 20(S)-protopanaxadiol | 10 | 10 | 4690.1 ± 332.1*** | 16.2 |
| 20(S)-protopanaxadiol | 1 | 10 | 4950.6 ± 534.5** | 11.5 |
| 20(S)-protopanaxadiol | 0.1 | 10 | 5137.2 ± 465.7* | 8.2 |
| 20(S)-protopanaxadiol | 0.01 | 10 | 5347.8 ± 555.1 | 4.4 |

Note:
dosed groups compared with the control group: *p < 0.05, p < 0.01, *p < 0.001.

As shown in Table 14, 20(S)-protopanaxadiol at concentrations of 10, 1 and 0.1 μg/ml extremely significantly, significantly and remarkably inhibited the re-uptake of NA (P<0.05, P<0.01, P<0.001), respectively. The respective inhibitory rates were 16.2%, 11.5% and 8.2%.

Conclusion (1) Anti-depression Animal Model Tests (i) Results with a depression model of reserpine-induced ptosis indicated that a 15 mg/kg dose of 20(S)-protopanaxadiol remarkably inhibited ptosis induced by reserpine in multiple-dose testing (10-day course).

(ii) Results with a depression model of reserpine-induced akinesia indicated that at a dose of 15 mg/kg, 20(S)-protopanaxadiol remarkably inhibited akinesia induced by reserpine in multiple-dose testing (10-day course).

(iii) Results of the tail suspension test with mice indicated that the duration of immobility was remarkably decreased at a dose of 15 mg/kg 20(S)-protopanaxadiol in single-dose tests. Doses of 15, 7.5 and 3.75 mg/kg of 20(S)-protopanaxadiol significantly or remarkably decreased the duration of immobility in all dosed groups on multiple-dose testing (10-day course).

(iv) Results of the forced swimming test using mice indicated that the duration of immobility within the 4 minutes swimming time was significantly or remarkably decreased at a single dose of 15, 7.5 and 3.75 mg/kg of 20(S)-protopanaxadiol. Results of multiple-dose tests (10-day course) at dosage of 15, 7.5 and 3.75 mg/kg of 20(S)-protopanaxadiol showed the same tendency.

(v) Chronic unpredictable stress testing of rats indicated that the number of rearing of rats in the groups treated with 20(S)-protopanaxadiol at 13.33 and 6.67 mg/kg doses were extremely significantly or significantly increased. The number of crossing of rats was also significantly or remarkably increased at these doses.

(vi) Stress testing of rats wearing shackles indicated that the number of rearing and crossing of rats administered 20(S)-protopanaxadiol at 13.33 and 6.67 mg/kg doses were extremely significantly or significantly increased, and the number of rearing at a dose of 3.33 mg/kg were remarkably increased. The level of NE was remarkably increased in rats administered 20(S)-protopanaxadiol at a dose of 6.67 mg/kg. The levels of NE, 5-HT and HAV were remarkably increased in rats administered 20(S)-protopanaxadiol at a dose of 3.33 mg/kg.

(2) The anti-depression pharmacological analysis indicated that 20(S)-protopanaxadiol remarkably enhanced 5-HTP induced tremors or behavioral effects of levodopa at doses of 15 and 7.5 mg/kg; 20(S)-protopanaxadiol at concentrations of 10, 1 and 0.1 μg/ml had extremely significant, significant or remarkable inhibitory effects on 5-HT and NA re-uptake respectively.

In view of its effects on anti-depression, 20(S)-protopanaxadiol with effects on anti-depression can be used in the preparation of medicaments for the treatment of depressive psychiatric disorders, such as depressive episode, recurrent depression, bipolar affective disorder and persistent affective disorder.

INDUSTRIAL APPLICATION

The invention relates to the use of 20(S)-protopanaxadiol in the preparation of medicaments for the treatment of depressive psychiatric disorders. The pharmacological test results indicated that the compound remarkably increased levels of NE, 5-HT and HAV in brains of model rats; remarkably enhanced 5-HTP-induced-tremor and LEVODOPA-induced-behavior and inhibited the re-uptake of 5-HT and NA.

The invention claimed is:

1. A method for the treatment of a depressive psychiatric disorder in a mammal consisting essentially of applying to the mammal a pharmaceutical composition comprising 20(S)-protopanaxadiol and a pharmaceutically acceptable additive.

2. The method according to claim 1, wherein the depressive psychiatric disorder is selected from the group consisting of depressive episode, recurrent depression, bipolar affective disorders and persistent affective disorders.

3. The method according to claim 2, wherein the depressive episode is mild, intermediate or severe.

4. The method according to claim 1, wherein the pharmaceutical composition is formulated in a form of an orally administrable solution, an injectable solution, a tablet, a capsule, a pill or granules.

5. The method according to claim 1, wherein the pharmaceutical acceptable additive is selected from the group consisting of solvent, emulsifier, sweetener, salt, adhesive, or a combination thereof.

6. The method according to claim 5, wherein the solvent is water, ethanol, or a combination thereof.

7. The method according to claim 5, wherein the emulsifier is Tween, Span, or a combination thereof.

8. The method according to claim 5, wherein the sweetener is sucrose, lactose, or a combination thereof.

9. The method according to claim 5, wherein the salt is magnesium stearate, CMCNa, sodium chloride, or a combination thereof.

10. The method according to claim 7, wherein the pharmaceutical composition comprises 20(S)-protopanaxadiol in a suspension of 0.3% sodium carboxymethyl cellulose (CMCNa)/Tween-80 solution.

11. The method according to claim 8, wherein the pharmaceutically acceptable additives are a combination of lactose, ethanol, water and magnesium stearate.

12. The method according to claim 1, wherein the pharmaceutical composition is administered orally or by injection.

13. The method according to claim 1, wherein the dosage of the medicament is 0.83 mg/kg 20(S)-protopanaxadiol, 3.33 mg/kg 20(S)-protopanaxadiol, 3.75 mg/kg 20(S)-protopanaxadiol, 6.67 mg/kg 20(S)-protopanaxadiol, 7.5 mg/kg 20(S)-protopanaxadiol, 13.33 mg/kg 20(S)-protopanaxadiol, or 15 mg/kg 20(S)-protopanaxadiol.

14. The method according to claim 11, wherein the pharmaceutical composition is administered orally, and the oral dosage per day is about 0.83 mg/kg 20(S)-protopanaxadiol, 3.33 mg/kg 20(S)-protopanaxadiol, 3.75 mg/kg 20(S)-protopanaxadiol, 6.67 mg/kg 20(S)-protopanaxadiol, 7.5 mg/kg 20(S)-protopanaxadiol, 13.33 mg/kg 20(S)-protopanaxadiol, or 15 mg/kg 20(S)-protopanaxadiol.

15. The method according to claim 12, wherein the pharmaceutical composition comprises 20(S)-protopanaxadiol in a suspension of 0.3% CMCNa/Tween-80 solution.

16. The method according to claim 12, wherein the pharmaceutically acceptable additives are a combination of lactose, ethanol, water and magnesium stearate.

17. The method according to claim 1, wherein the pharmaceutical composition is administered once a day.

18. The method according to claim 12, wherein the pharmaceutical composition is administered once a day.

19. The method according to claim 13, wherein the pharmaceutical composition is administered once a day.

20. The method according to claim 14, wherein the pharmaceutical composition is administered once a day.

* * * * *